(12) United States Patent
Lineaweaver

(10) Patent No.: US 8,265,767 B2
(45) Date of Patent: Sep. 11, 2012

(54) STOCHASTIC STIMULATION IN A HEARING PROSTHESIS

(75) Inventor: Sean Lineaweaver, Parker, CO (US)

(73) Assignee: Cochlear Limited, Macquarie University, NSW (AU)

( * ) Notice: Subject to any disclaimer, the term of this patent is extended or adjusted under 35 U.S.C. 154(b) by 593 days.

(21) Appl. No.: 12/403,949

(22) Filed: Mar. 13, 2009

(65) Prior Publication Data
US 2009/0319005 A1 Dec. 24, 2009

Related U.S. Application Data

(60) Provisional application No. 61/036,318, filed on Mar. 13, 2008.

(51) Int. Cl.
*A61N 1/36* (2006.01)

(52) U.S. Cl. .................... 607/57; 607/1; 607/2; 607/55; 607/56; 607/73

(58) Field of Classification Search .................. 607/1–2, 607/55–57, 73
See application file for complete search history.

(56) References Cited

U.S. PATENT DOCUMENTS

| | | | |
|---|---|---|---|
| 6,907,130 B1 | 6/2005 | Rubinstein et al. | |
| 7,231,257 B2 | 6/2007 | McDermott et al. | |
| 7,885,714 B2 * | 2/2011 | Loeb | 607/57 |
| 8,000,797 B1 * | 8/2011 | Sarpeshkar et al. | 607/57 |

OTHER PUBLICATIONS

Yost et al., "Pitch Strength of Regular-Interval Click Trains with Different Length Runs of Regular Intervals," Journal of Acoustical Society of America 117(5), May 2005, pp. 3054-3068.

Krumbholz et al., "The Effect of Cross-Channel Synchrony on the Perception of Temporal Regularity," Acoustical Society of America 118(2), Aug. 2005, pp. 946-954.

Wieringen et al., "Pitch of Amplitude-Modulated Irregular-Rate Stimuli in Acoustic and Electric Hearing," Journal of Acoustical Society of America 114(3), Sep. 2003, pp. 1516-1528.

Collins et al., "Temporal Pattern Discrimination and Speech Recognition under Electrical Stimulation," Journal of Acoustical Society of America 96(5), Pt. 1, Nov. 1994, pp. 2731-2737.

Roberts et al., "Primitive Stream Segregation of Tone Sequences without Differences in Fundamental Frequency or Passband," Journal of Acoustical Society of America 112(5), Pt. 1, Nov. 2002, pp. 2074-2085.

Kaernbach et al., "Psychophysical Evidence Against the Autocorrelation Theory of Auditory Temporal Processing," Journal of Acoustical Society of America 104 (4), Oct. 1998, pp. 2298-2306.

Carlyon et al., "Temporal Pitch Mechanisms in Acoustic and Electric Hearing," Journal of Acoustical Society of America 112 (2), Aug. 2002, pp. 621-633.

* cited by examiner

*Primary Examiner* — Carl H Layno
*Assistant Examiner* — Deborah Malamud
(74) *Attorney, Agent, or Firm* — Kilpatrick Townsend & Stockton, LLP

(57) ABSTRACT

A hearing prosthesis configured for delivery of stochastic stimulation to a recipient. The hearing prosthesis comprises a sound pickup component configured to receive a sound signal having at least one pitch; a stochastic stimulation generator configured to generate a stochastic sequence of stimulation pulses having first and second inter-pulse intervals distributed stochastically throughout the sequence within controlled limits, the first inter-pulse interval based on the at least one pitch; and at least one stimulation channel to deliver the sequence of electrical stimulation pulses to the recipient.

29 Claims, 12 Drawing Sheets

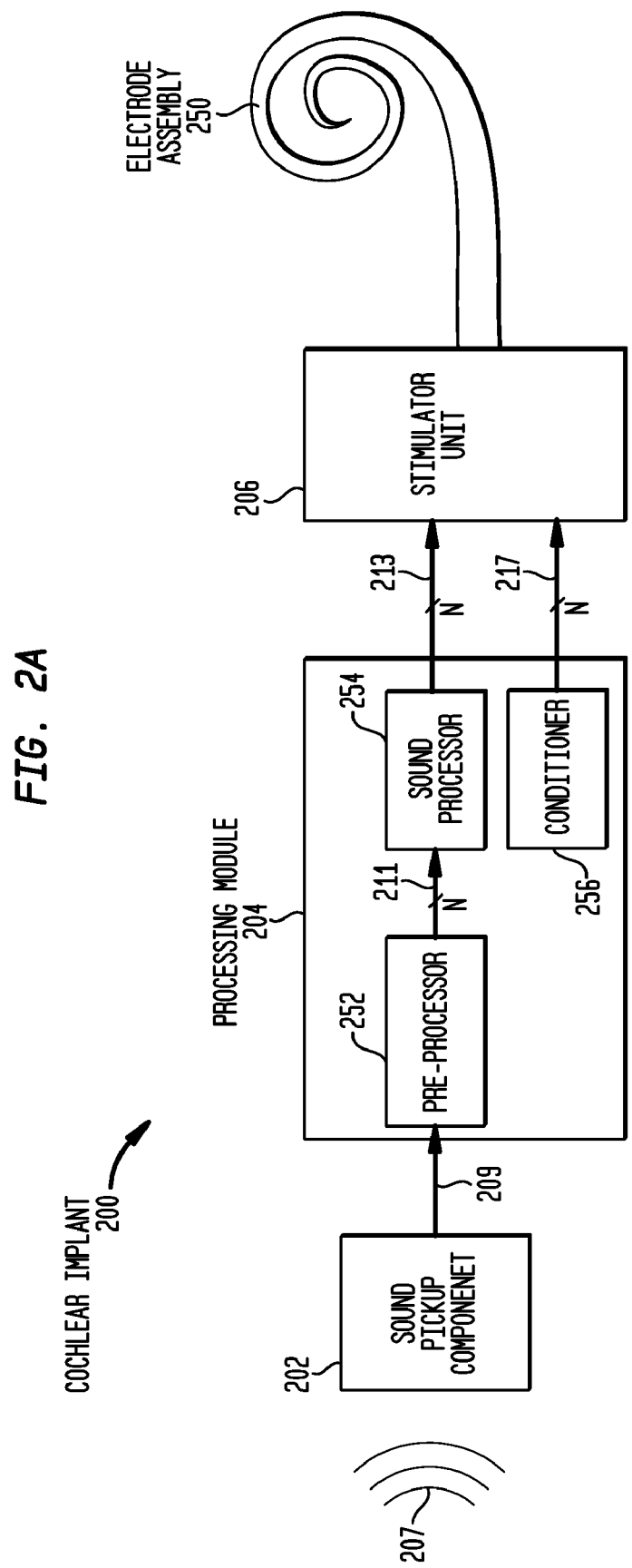

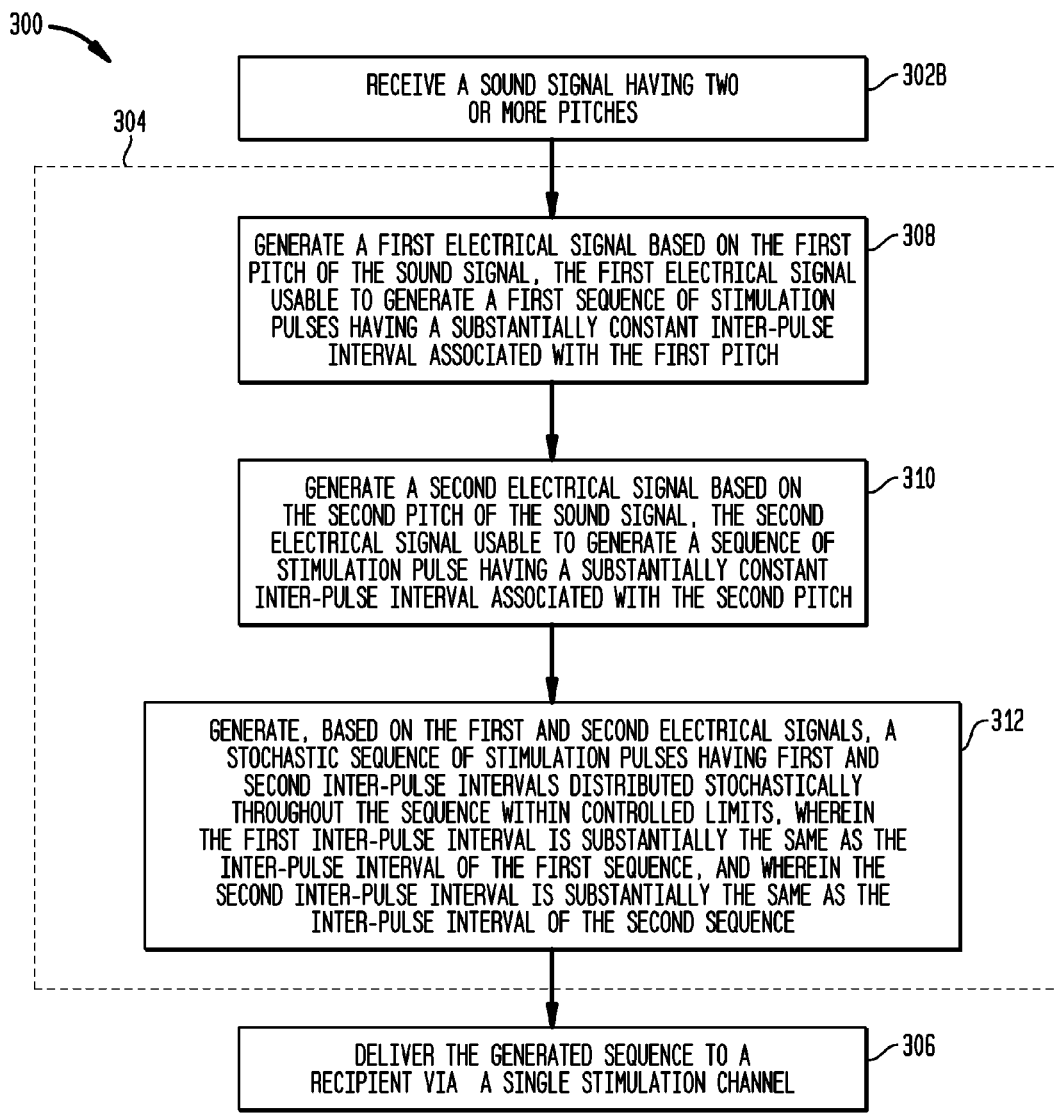

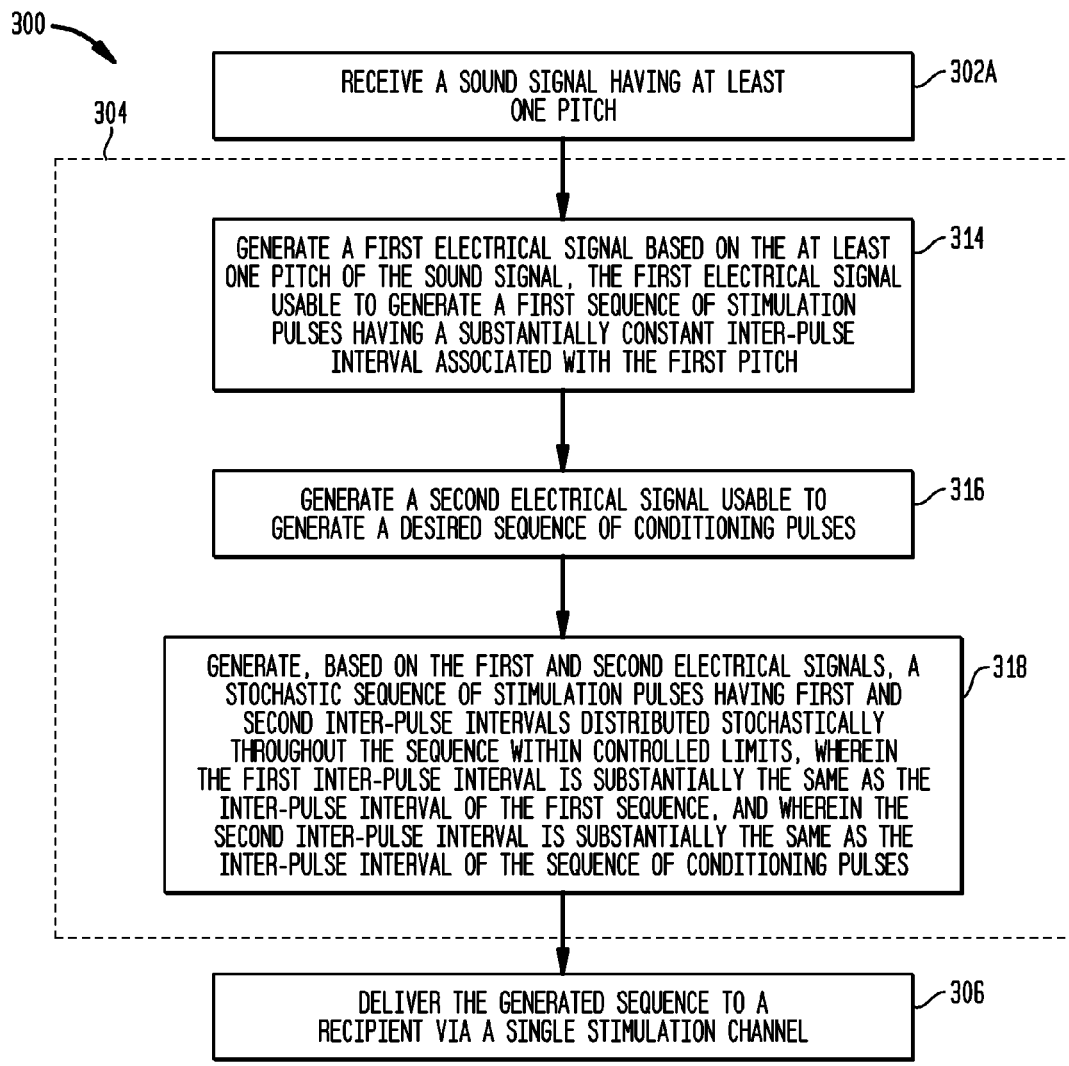

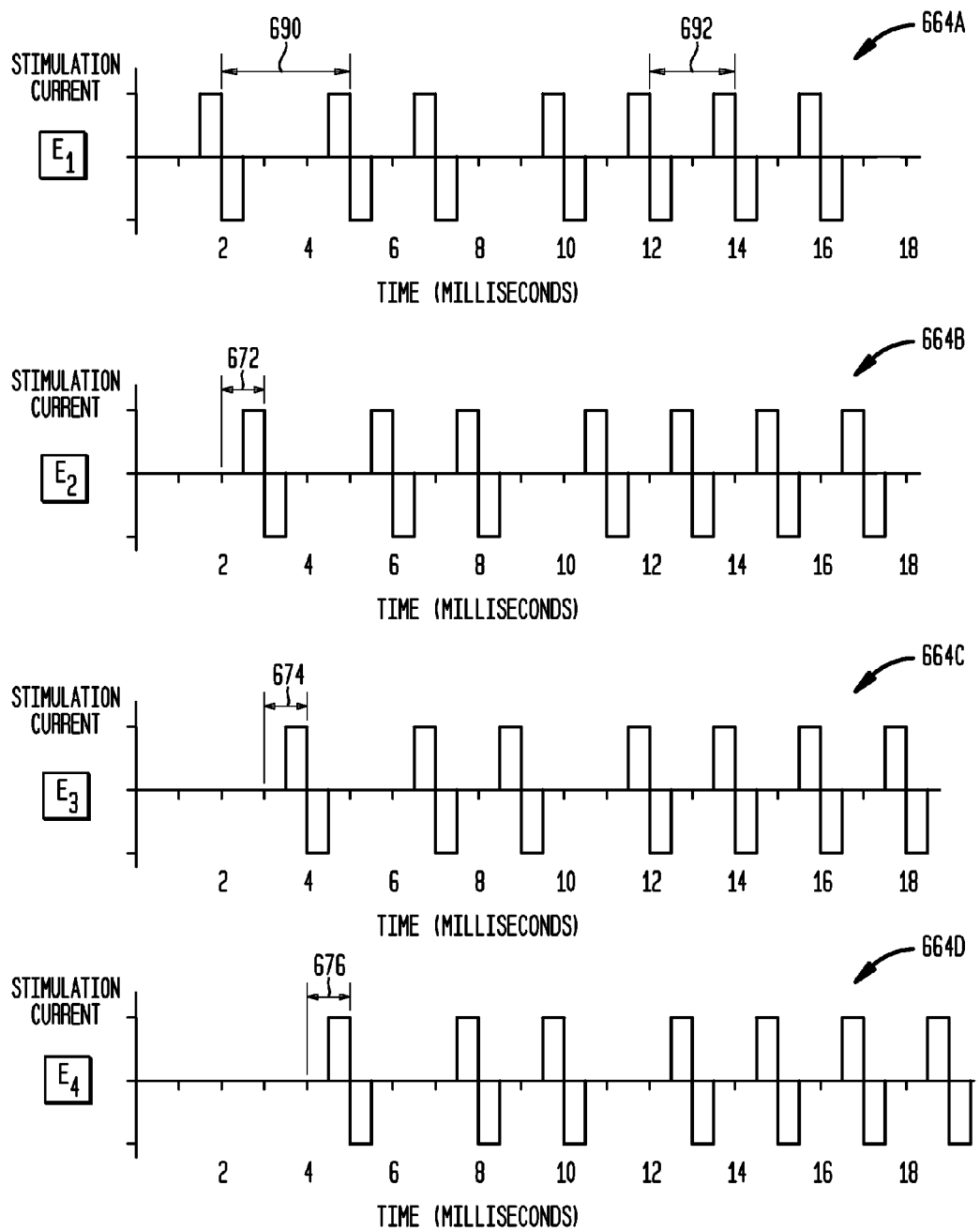

STOCHASTIC STIMULATION IN A HEARING PROSTHESIS

CROSS-REFERENCE TO RELATED APPLICATIONS

The present application claims the benefit of U.S. Provisional Patent Application 61/036,318; filed Mar. 13, 2008, which is hereby incorporated by reference herein.

BACKGROUND

1. Field of the Invention

The present invention is generally directed to a hearing prosthesis, and more particularly, to stochastic stimulation in a hearing prosthesis.

2. Related Art

Hearing loss, which may be due to many different causes, is generally of two types, conductive and sensorineural. In some cases, a person suffers from hearing loss of both types. Conductive hearing loss occurs when the normal mechanical pathways for sound to reach the cochlea, and thus the sensory hair cells therein, are impeded, for example, by damage to the ossicles. Individuals who suffer from conductive hearing loss typically have some form of residual hearing because the hair cells in the cochlea are undamaged. As a result, individuals suffering from conductive hearing loss typically receive an acoustic hearing aid. Acoustic hearing aids stimulate an individual's cochlea by providing an amplified sound to the cochlea that causes mechanical motion of the cochlear fluid.

In many people who are profoundly deaf, however, the reason for their deafness is sensorineural hearing loss. Sensorineural hearing loss occurs when there is damage to the inner ear, or to the nerve pathways from the inner ear to the brain. As such, those suffering from some forms of sensorineural hearing loss are thus unable to derive suitable benefit from conventional acoustic hearing aids. As a result, hearing prostheses that deliver electrical stimulation to nerve cells of the recipient's auditory system have been developed to provide the sensations of hearing to persons whom do not derive adequate benefit from conventional hearing aids. Such electrically-stimulating hearing prostheses deliver electrical stimulation to nerve cells of the recipient's auditory system thereby providing the recipient with a hearing percept.

As used herein, the recipient's auditory system includes all sensory system components used to perceive a sound signal, such as hearing sensation receptors, neural pathways, including the auditory nerve and spiral ganglion, and parts of the brain used to sense sounds. Electrically-stimulating hearing prostheses include, for example, auditory brain stimulators and Cochlear™ prostheses (commonly referred to as Cochlear™ prosthetic devices, Cochlear™ implants, Cochlear™ devices, and the like; simply "cochlear implants" herein.)

Oftentimes, sensorineural hearing loss is due to the absence or destruction of the cochlear hair cells which transduce acoustic signals into nerve impulses. It is for this purpose that cochlear implants have been developed. Cochlear implants provide a recipient with a hearing percept by delivering electrical stimulation signals directly to the auditory nerve cells, thereby bypassing absent or defective hair cells that normally transduce acoustic vibrations into neural activity. Such devices generally use an electrode array implanted in the cochlea so that the electrodes may differentially activate auditory neurons that normally encode differential pitches of sound.

Both cochlear implants and hearing aids provide a recipient with a hearing percept by stimulating the cochlea of an individual or patient (collectively referred to as recipient herein) with digital stimulation signals. These stimulation signals may be, for example, electrical pulses delivered directly to the cochlea via the electrode assembly of the cochlear implant, or acoustic information delivered indirectly to the cochlea via the outer and middle ear of the recipient from the output transducer of the hearing aid.

SUMMARY

In one aspect of the invention, a method for providing a hearing percept to a recipient of a hearing prosthesis is provided. The method comprises: receiving a sound signal having at least one pitch; generating a stochastic sequence of stimulation pulses having first and second inter-pulse intervals distributed stochastically throughout the sequence within controlled limits, the first inter-pulse interval based on the at least one pitch; and delivering the generated stochastic sequence to the recipient via a single stimulation channel of the hearing prosthesis.

In another aspect of the invention, a hearing prosthesis is provided. The method comprises: a sound pickup component configured to receive a sound signal having at least one pitch; a stochastic stimulation generator configured to generate a stochastic sequence of stimulation pulses having first and second inter-pulse intervals distributed stochastically throughout the sequence within controlled limits, the first inter-pulse interval based on the at least one pitch; and at least one stimulation channel to deliver the sequence of electrical stimulation pulses to the recipient.

BRIEF DESCRIPTION OF THE DRAWINGS

Illustrative embodiments of the present invention are described herein with reference to the accompanying drawings, in which:

FIG. 2A is a functional block diagram of a cochlear implant in accordance with embodiments of the present invention;

FIG. 3B is a detailed flowchart illustrated the operations performed by a hearing prosthesis in accordance with one embodiment of FIG. 3B;

FIG. 3C is a detailed flowchart illustrated the operations performed by a hearing prosthesis in accordance with another embodiment of FIG. 3B;

FIG. 6B is a graph of stimulation current versus time that illustrate the delivery of a synchronized stochastic stimulation signal to a cochlea of a recipient via four electrodes of a cochlear implant in accordance with embodiments of FIG. 2B;

DETAILED DESCRIPTION

Aspects of the present invention are generally directed to stochastic stimulation in a hearing prosthesis. Specifically, a stochastic sequence of stimulation signals is generated and delivered to the recipient. The sequence of signals comprises electrical, mechanical or acoustical pulses generated and delivered to the inner, middle, or outer ear of cochlea of the recipient. The pulses within the sequence have controlled randomness in the pulse timing. That is, the time intervals between immediately adjacent pulses (referred to as inter-pulse intervals herein) are selected stochastically within controlled limits.

Figure 1:
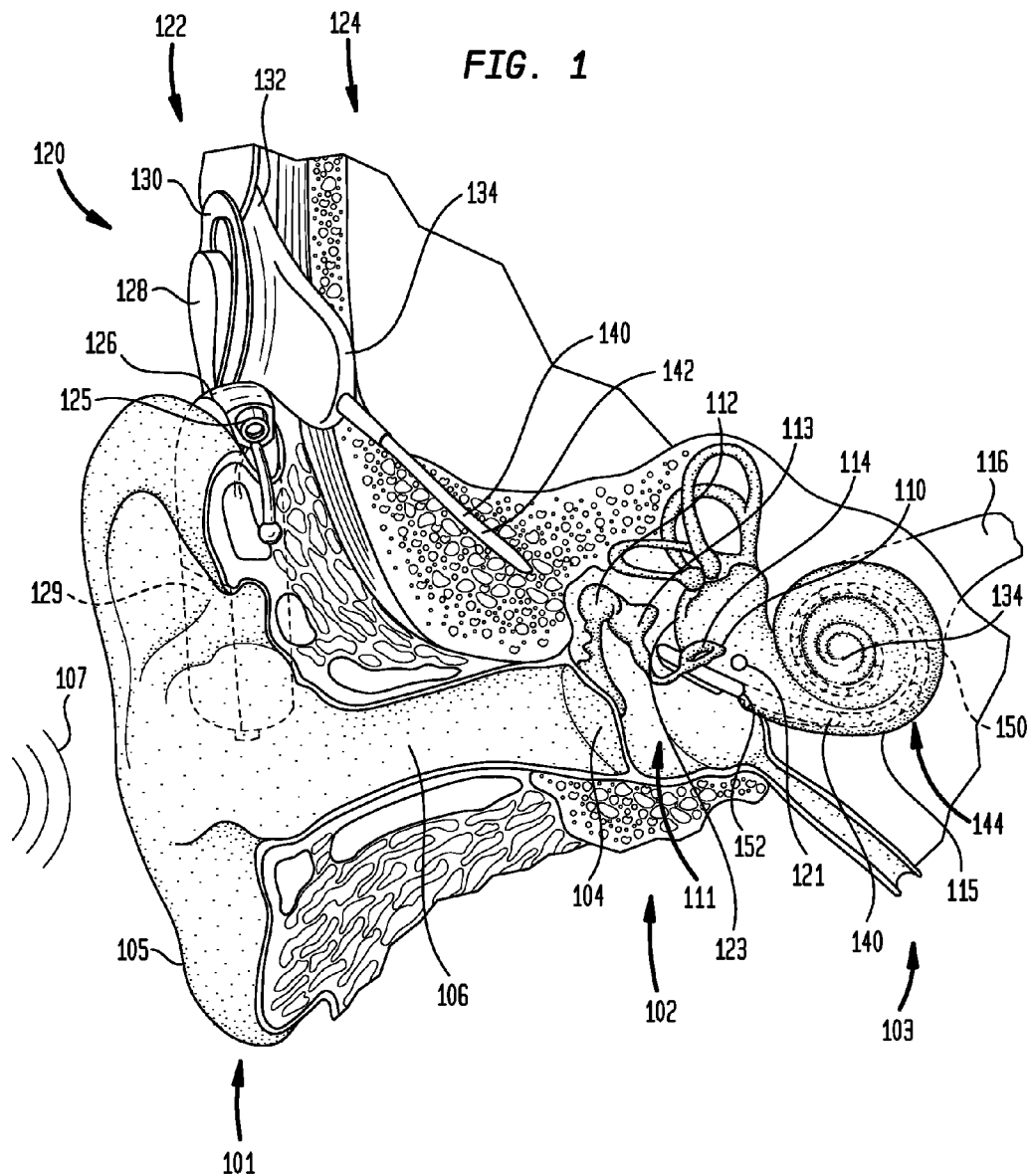
FIG. 1 is a perspective view of an exemplary hearing prosthesis, a cochlear implant, in which embodiments of the present invention may be advantageously implemented.

Embodiments of the present invention may be implemented in various types of hearing prostheses such as a Cochlear™ prosthesis (commonly referred to as a Cochlear™ prosthetic device, Cochlear™ implant, Cochlear™ device, and the like; simply "cochlear implants" herein), middle ear transducers or acoustic hearing aids. For ease of illustration, the present invention will be described herein primarily in connection with cochlear implants. FIG. 1 is a perspective view of an exemplary cochlear implant 120 in which embodiments of the present invention may be implemented. The relevant components of the recipient's ear are described below, followed by a description of cochlear implant 120.

In fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 110 through three bones of middle ear 102, collectively referred to as the ossicles 111 and comprising the malleus 112, the incus 113 and the stapes 114. Bones 112, 113 and 114 of middle ear 102 serve to filter and amplify acoustic wave 107, causing oval window 110 to articulate, or vibrate. Such vibration sets up waves of fluid motion within cochlea 115. Such fluid motion, in turn, activates tiny hair cells (not shown) that line the inside of cochlea 115. Activation of the hair cells causes appropriate nerve impulses to be transferred through the spiral ganglion cells and auditory nerve 116 to the brain (not shown), where they are perceived as sound. In certain profoundly deaf persons, there is an absence or destruction of the hair cells. Cochlear implants such as cochlear implant 120 are utilized to stimulate the ganglion cells to cause a hearing percept.

Cochlear implant 120 comprises external component 122 which is directly or indirectly attached to the body of the recipient, and an internal component 124 which is temporarily or permanently implanted in the recipient. External component 122 comprises a sound pickup component, such as microphone 125, for detecting sound. The sound detected by microphone 125 is output to a behind-the-ear (BTE) speech processing unit 126 that generates coded signals which are provided to an external transmitter unit 128, along with power from a power source 129 such as a battery. External transmitter unit 128 comprises an external coil 130 and, preferably, a magnet (not shown) secured directly or indirectly in external coil 130.

Internal component 124 comprise an internal coil 132 of a stimulator unit 134 that receives and transmits power and coded signals received from external component 122 to other elements of stimulator unit 134 which apply the coded signal to cochlea 115 via an implanted electrode assembly 140. Elongate electrode assembly 140 has a proximal end connected to stimulator unit 134, and a distal end implanted in cochlea 115. In some embodiments electrode assembly 140 may be implanted at least in basal region 116, and sometimes further. For example, electrode assembly 140 may extend towards apical end of cochlea 115, referred to as cochlea apex 134. In certain circumstances, electrode assembly 140 may be inserted into cochlea 115 via a cochleostomy 152. In other circumstances, a cochleostomy may be formed through round window 121, oval window 110, the promontory 123 or through an apical turn of cochlea 115.

Electrode assembly 140 comprises a longitudinally aligned and distally extending array 144 of electrodes 150, sometimes referred to as electrode array 144 herein, disposed along a length thereof. Although electrode array 144 may be disposed on electrode assembly 140, in most practical applications, electrode array 144 is integrated into electrode assembly 140. As such, electrode array 144 is referred to herein as being disposed in electrode assembly 140. Stimulator unit 134 generates stimulation signals which are applied by electrodes 150 to cochlea 115, thereby stimulating auditory nerve 116.

Although FIG. 1 illustrates a cochlear implant 120 having an external component 122, it should be appreciated that embodiments of the present invention may be implemented in other cochlear implant embodiments, such as a totally implantable cochlear implant.

As noted, aspects of the present invention are generally directed to generating and delivering a discrete stochastic sequence of stimulation signals to a recipient. In cochlear implants, the sequence comprises electrical stimulation pulses delivered to cochlea 115 via a single implanted electrode. The intervals between immediately adjacent pulses (referred to as inter-pulse intervals herein) are selected stochastically within controlled limits. The distribution of inter-pulse intervals within a stochastic sequence of the present invention is discussed in greater detail below.

Delivering a stochastic sequence of electrical stimulation signals to a recipient via a single electrode may provide various benefits that are not possible in conventional systems. As is well known in the art, a recipient's cochlea is "tonotopically mapped." In other words, basal region 116 of cochlea 115 is responsive to high frequency signals, while regions of the recipient's cochlea 115 closer to cochlear apex 134 are responsive to low frequency signals. To enhance perception of sounds, conventional cochlear implants exploit these tonotopical properties of cochlea 115 by delivering stimulation signals within a predetermined frequency range to a region of the cochlea that is most sensitive to that particular frequency range. For example, the frequency of a sound, sometimes referred to as pitch herein, is perceivable to the recipient by delivering stimulation signals representing the pitch via an electrode positioned at the location of cochlea 115 that is most sensitive to the selected pitch.

In certain conventional cochlear implants, multiple pitches may be perceived by a recipient by delivering stimulation signals to the recipient via spatially separated electrodes. That is, a first set of one or more stimulation signals is delivered to the recipient via a first electrode, while a second set of stimulation signals is delivered to the recipient via a second electrode that is spatially separated from the first electrode. The signals may be delivered simultaneous or sequentially to cause perception of the two different pitches. As would be appreciated, a drawback of such conventional systems is that different electrodes must be used for each desired pitch.

Embodiments of the present invention avoid the above and other drawbacks of conventional systems by exploiting the ability of cochlea 115 to temporally segregate pitches. Specifically, as noted above, a stochastic sequence of electrical stimulation pulses is generated and delivered to the recipient via a single electrode. The sequence comprises pulses separated by two or more inter-pulse intervals that are distributed stochastically throughout the sequence within controlled limits. This controlled randomness in the pulse timing exploits the temporal pitch perception properties of the cochlea so that multiple pitches may be perceived as a result of the single stochastic pulse sequence. This ability may enhance speech processing and/or sound coding strategies implemented by a cochlear implant.

For example, in certain embodiments, the cochlear implant may receive a sound signal generated by first and second sound sources having first and second pitches, respectively. In these embodiments, a stochastic sequence of electrical stimulation pulses in accordance with embodiments of the present invention is generated. The sequence comprises pulses separated by a first inter-pulse interval based on the first pitch, and pulses separated by a second inter-pulse interval based on the second pitch. As noted, the first and second inter-pulse intervals are stochastically distributed throughout the sequence within controlled limits. Upon delivery of the stochastic stimulation sequence, the recipient may differentiate sounds from the first and second sources.

In alternative embodiments, the first and second pitches are not necessarily obtained from two sources. For example, the first and second pitches may comprise different pitch components of a sound signal, regardless of the source of the signal.

In other embodiments of the present invention, the cochlear implant is configured to deliver a conditioning stimulus to the recipient. The conditioning stimulus comprises a sequence of pulses delivered to the recipient at a high rate. A cochlear implant in accordance with embodiments of the present invention may encode a conditioning sequence within a pulse sequence representing a pitch of a received sound signal. Specifically, in such embodiments, a stochastic sequence of electrical stimulation pulses having a first inter-pulse interval based on the pitch of a received sound signal, and a second inter-pulse interval based on a conditioning sequence is generated. As noted, the first and second inter-pulse intervals are stochastically distributed throughout the sequence within controlled limits. Thus, the generated sequence permits conditioning and sound perception at a single electrode.

FIG. 2A is a functional block diagram illustrating embodiments of cochlear implant 120 of FIG. 1, referred to as cochlear implant 200 herein. Cochlear implant 200 comprises a sound pickup component 202, a processing module 204, a stimulator unit 206 and an electrode assembly 250. Sound pickup component 202 is configured to receive a sound signal 207. Sound pickup component 202 may comprise, for example, one or more microphones, a telecoil, or an electrical input which connects cochlear implant 200 to FM hearing systems, MP3 players, musical instruments, computers, televisions, mobile phones, etc. As such, sound signal 207 may comprise a sound wave or an electrical audio signal. In the embodiment of FIG. 2A, sound pickup component 202 comprises a microphone 202 which may be a directional microphone and/or an omni-directional microphone. Sound pickup component 202 outputs signals 209 representing received sound signal 207 to processing module 204.

As shown, processing module 204 comprises a pre-processor 252, a sound processor 254, and a conditioner 256. Pre-processor 252 converts signals 209 output by sound pickup component 202 into digital signals 211 representing the received sound. Digital signals 211 are provided to sound processor 254. Pre-processor 252 is shown in FIG. 2A as an element of processing module 204. As would be appreciated, in certain embodiments of the present invention, pre-processor 252 may be implemented by sound pickup module 202. In these embodiments, sound pickup module 202 would output digital signals directly to sound processor 254.

Signals 211 are converted by processing module 254 into data signals 213. As described in greater detail below, data signals 213 may be utilized by stimulator unit 206 to generate a stochastic sequence of electrical stimulation pulses that are delivered to the recipient's cochlea via electrode assembly 250.

As noted, processing module further includes conditioner 256. As described in greater detail below, in certain embodiments conditioner 256 generates conditioning signals 217 which are utilized by stimulator unit 206 to generate a stochastic sequence of electrical stimulation pulses.

Figure 2B:
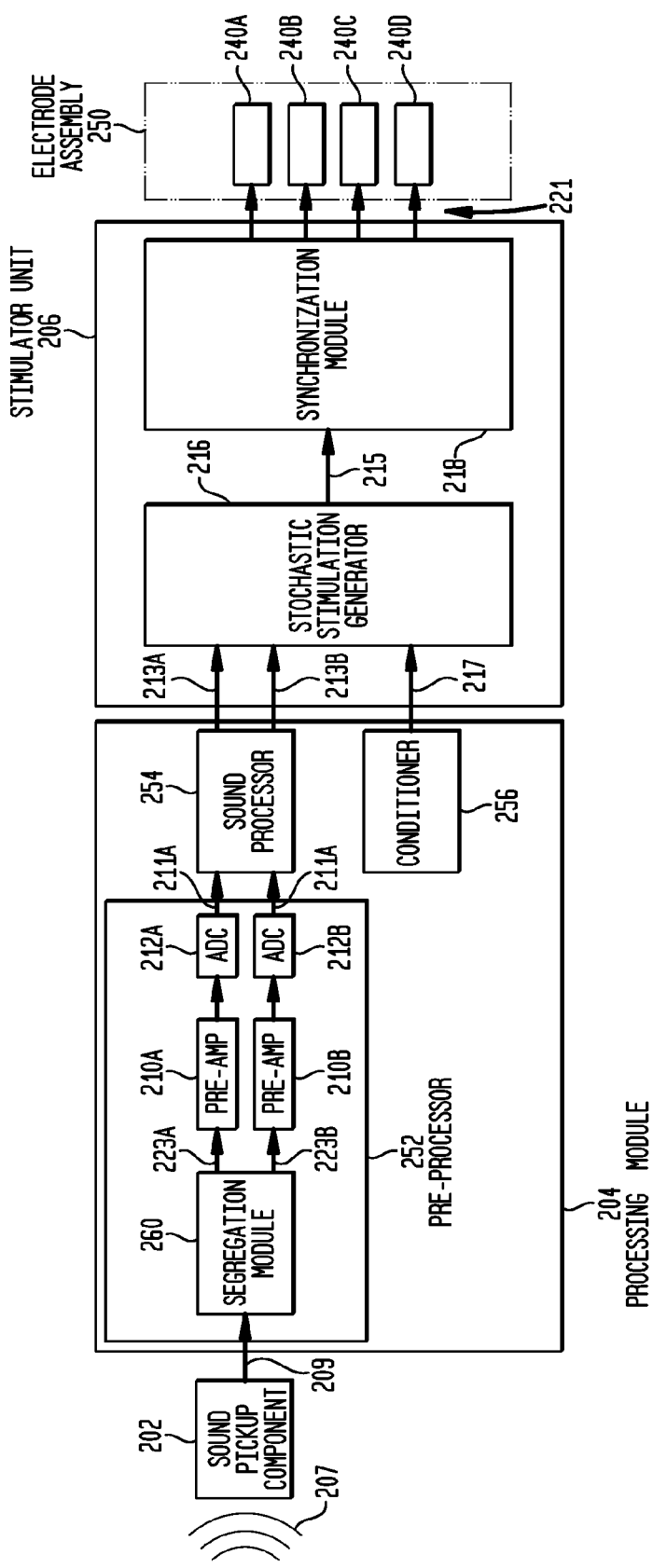
FIG. 2B is a detailed functional block diagram of the cochlear implant of FIG. 2A.

FIG. 2B is a detailed functional block diagram illustrating the components of cochlear implant 200 in accordance with one embodiment of the present invention. As noted above, cochlear implant 200 comprises sound pickup component 202, processing module 204, stimulator 206 and electrode assembly 250.

As noted, signals 209 from sound pickup component 202 are provided to pre-processor 252. As noted above, embodiments of the present invention are configured to generate a stochastic sequence of electrical stimulation pulses resulting in the perception of two or more pitches by the recipient. In such embodiments, pre-processor 252 comprises a segregation module 260 which separates signals 209 into components 223A corresponding to a first pitch within sound signal 207, and components 223B corresponding to a second pitch within sound signal 207. As noted above, the first and second pitches may correspond to different sources, different pitch components of a sound signal regardless of the source, etc.

Pre-processor 252 also comprises two each of preamplifiers/automatic gain controllers 210 and Analog-to Digital-Converters (ADCs) 212. Electrical signal components 223A, 223B are provided to preamplifiers/automatic gain controllers 210 which amplify and control the level of the electrical signals. The electrical signals modified by preamplifiers/automatic gain controllers 210 are provided to ADCs 212. ADCs 212 convert the modified electrical signal into a stream of digital pulses 211A, 211B.

In the embodiment shown in FIG. 2B, segregation module 260, preamplifiers/automatic gain controllers 210 and ADCs 212 have been shown separated for ease of illustration. However, it should be appreciated that these components may be implemented in a single element. FIG. 2B has been described in reference to an illustrative embodiment comprising two each of preamplifiers/automatic gain controllers 210 and ADCs 212. It should be appreciated that more or less of these components may be provided and the embodiments of FIG. 2B are provided for illustrative purposes only. Furthermore, as noted above, in certain embodiments of the present invention, pre-processor 252 may be implemented as a component of sound pickup component 202.

It should also be appreciated that in certain embodiments, one or more components of pre-processor module 252 may not be necessary. For example, in certain embodiments, sound signal 207 received by sound pickup component may comprise a digitized signal received from, for example, a FM hearing system, MP3 player, television, mobile phones, etc. In these embodiments, the received signal may be processed by segregation module and provided to sound processor 254, or under certain circumstances, the signals may be provided directly to sound processor 254.

As shown in FIG. 2B, digital signals 211 are provided to sound processor 254 which comprises a digital sound processor. Sound processor 254 converts digital signals 211 into one or more data signals 213. In the embodiments of FIG. 2B, data signals 213 may be utilized by stimulator unit 206 to generate a stochastic sequence of electrical stimulation pulses. For example, in the illustrative embodiments, a first data signal 213A is generated based on components 223A of sound signal 207 corresponding to a first pitch. Data signal 213A is usable by stimulator unit 206 to generate a sequence of electrical stimulation pulses having a substantially constant inter-pulse interval that is based on the first pitch. Similarly, a second data signal 213B is generated based on components 223B of sound signal 207 corresponding to a second pitch. Data signal 213B is usable by stimulator unit 206 to generate a sequence of electrical stimulation pulses having a substantially constant inter-pulse interval that is based on the second pitch.

As noted above, generated signals 213 are provided to stimulator unit 206. Stimulator unit 206 comprises a stochastic stimulation generator 216 and a synchronization module 218. In the embodiment of FIG. 2B, signals 213 are provided to stochastic stimulation generator 216. Stochastic stimulation generator 216 generates a stochastic sequence of electrical stimulating pulses 215 having controlled randomness in the pulse timing. Pulse timing refers to distribution of inter-pulse intervals within the sequence. For example, each pulse in stochastic stimulation sequence 215 is separated in time from an immediately adjacent pulse by an inter-pulse interval selected stochastically within controlled limits. The controlled limits on the stochastic inter-pulse interval distribution are discussed below.

In the illustrative embodiment of FIG. 2B, stochastic stimulation generator 216 combines signals 213A and 213B to derive stochastic stimulation sequence 215. It should be appreciated that stochastic stimulation generator 216 may use a variety of methods, algorithms, etc. to derive stochastic stimulation 215 from signals 213. In one alternative embodiment of the present invention, a single set of signals 213 may be provided to stochastic stimulation generator 216. In this embodiment, stochastic stimulation sequence 215 may be derived from this single stimulation signal 213.

In certain embodiments of the present invention, stochastic stimulation sequence 215 is delivered to the recipient via a single electrode 240 of electrode assembly 250. Upon delivery of stochastic stimulation sequence 250, the recipient is able to perceive two pitches. For ease of illustration, electrode assembly 250 is shown schematically in FIG. 2B.

In certain embodiments of FIG. 2B, prior to delivery of stochastic stimulation sequence 215, synchronization module 218 synchronizes the delivery of sequence 215 across a plurality of electrodes 240. In other words, synchronization module 218 is configured to deliver the entirety of sequence 215 to each of a plurality of electrodes. This may enhance the perception of the two pitches. The delivery of the sequences to the plurality of electrodes may occur simultaneously or sequentially.

In the illustrated embodiment, stochastic stimulation generator 216 and synchronization module 218 have been shown separated from sound processor 254 as being integrated in stimulator unit 206. It should be appreciated that in certain embodiments of the present invention, stochastic stimulation generator 216 may be integrated with sound processor 254.

Electrode assembly 250 has been shown with four electrodes 240. However, it should be appreciated that more or less electrodes may be provided. For example, in certain embodiments, 22 electrodes may be provided to deliver stimulation to the recipient's cochlea.

As noted, processing module 204 also comprises conditioner 256. Conditioner 256 is configured to provide an instruction signal 217 to stochastic stimulation generator 216 indicating that a conditioning stimulus is desired or necessary. In these embodiments of the present invention, stochastic stimulation sequence 215 may be generated based on one or more signals 213 and signal 217. In such embodiments, stochastic stimulation 215 comprises a set of signals representing one or more pitches of a received sound, and a set of pulses which provide the desired conditioning stimulation.

As noted, the embodiments of the present invention have been discussed with reference to a received sound signal 207. As noted sound signal 207 may be received by sound pickup component which comprises one or more microphones, an electrical input, music instrument digital interface (MIDI), telecoil, etc. As such, the sound signal may comprise a sound wave or an electrical audio signal. In certain embodiments, the sound signal comprises music provided to the recipient via, for example, an MIDI file. In such embodiments, the pitches represented by the stochastic stimulation sequence comprise musical notes. Thus, embodiments of the present invention may permit a recipient to perceive multiple musical notes as a result of a single stimulation sequence delivered via a single electrode. This capability may provide a cochlear implant recipient with enhanced harmony and melody perception.

Figure 3A:
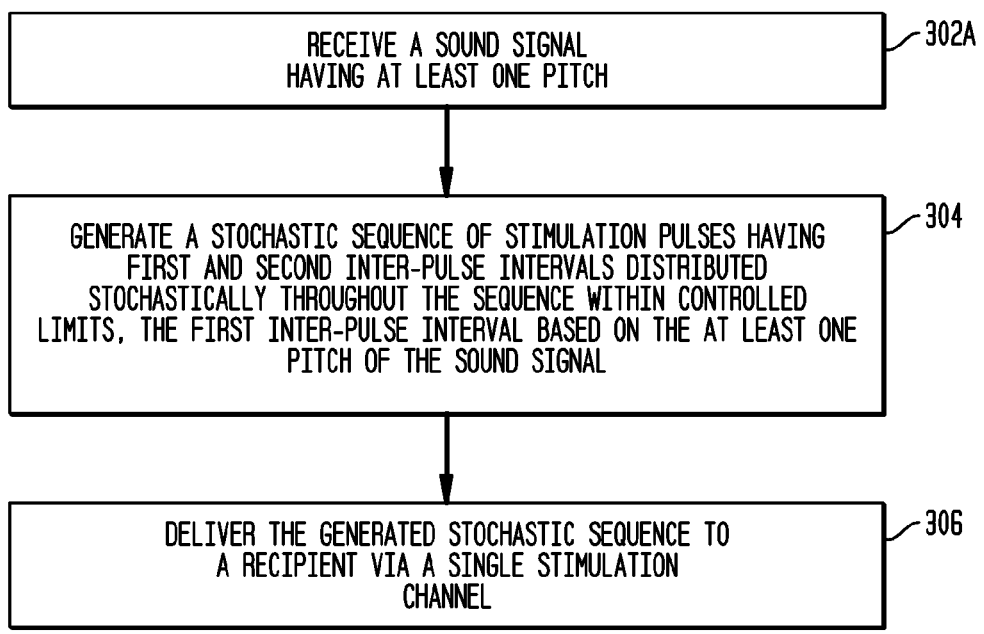
FIG. 3A is a high level flowchart illustrating the operations performed by a hearing prosthesis in accordance with embodiments of the present invention.

FIG. 3A is a flowchart illustrating a method 300 in accordance with embodiments of the present invention that may be implemented by a hearing prostheses to provide a hearing percept to a recipient of the hearing prosthesis. As shown, at block 302A a sound signal having at least one pitch is received by the hearing prosthesis. The sound signal may be received by a sound pickup component described above with reference to FIGS. 2A and 2B.

A block 304, a stochastic sequence of stimulation pulses is generated. The sequence comprises pulses first and second inter-pulse intervals distributed stochastically throughout the sequence within controlled or predetermined limits. That is, the timing of the pulses within the sequence is primarily stochastic, but fall within specified control parameters described in greater detail below. The first inter-pulse interval is based on the at least one pitch of the received sound.

At block 306, the generated sequence of stimulation pulses is delivered to the recipient via a single stimulation channel. As noted, embodiments of the present invention may be implemented in a variety of hearing prosthesis now known or later developed such as cochlear implants, acoustic hearing aids, etc. In the case of cochlear implants, the single stimulation channel terminates in a single electrode implanted in the recipient's cochlea. In the case of other types of hearing prosthesis, a single stimulation channel refers to a single output acoustic or mechanical transducer.

FIG. 3B is a detail level flowchart illustrating the operations performed at block 304 in accordance with one embodiment of FIG. 3A. As noted above, a sound signal is first received at block 302. In this embodiment, the sound signal has two or more pitches rather than at least one pitch, thus block 302 is referred to as block 302B.

As noted above, at block 304 a stochastic sequence of stimulation pulses is generated. In this illustrative embodiment, at block 308 a first electrical signal based on a first pitch of the received sound signal is generated. The first electrical signal is usable by the hearing prosthesis to generate a first sequence of stimulation pulses that have a substantially constant inter-pulse interval associated with the first pitch of the sound signal. At block 310, a second electrical signal based on a second pitch of the received sound signal is generated. The second electrical signal is usable by the hearing prosthesis to generate a second sequence of stimulation pulses that have a substantially constant inter-pulse interval associated with the second pitch of the sound signal.

At block 312, the first and second electrical signals generated at blocks 308, 310, respectively, are used to generate a stochastic sequence of stimulation pulses having first and second inter-pulse intervals. In this illustrative embodiment, the first inter-pulse interval is substantially the same as the inter-pulse interval of the first sequence of pulses corresponding to the first electrical signal, while the second inter-pulse interval is substantially the same as the inter-pulse interval of the second sequence of pulses corresponding to the second electrical signal. At block 306, the generated sequence of stimulation pulses is delivered to the recipient via a single stimulation channel.

FIG. 3C is a detail level flowchart illustrating the operations performed at block 304 in accordance with one embodiment of FIG. 3A. In these embodiments, the hearing prosthesis is configured to provide sequences of conditioning pulses to the recipient. As noted above, a sound signal having at least one pitch is first received at block 302A. As noted above, at block 304 a discrete sequence of stimulation pulses is generated.

In this illustrative embodiment, at block 314 a first electrical signal based on the at least one pitch of the received sound signal is generated. The first electrical signal is usable by the hearing prosthesis to generate a first sequence of stimulation pulses that have a substantially constant inter-pulse interval that is associated with the at least one pitch of the sound signal. At block 316, a second electrical signal usable to generate a desired sequence of conditioning pulses is generated.

At block 318, the first and second electrical signals generated at blocks 314, 316, respectively, are used to generate a sequence of stimulation pulses having first and second inter-pulse intervals. In this illustrative embodiment, the first inter-pulse interval is substantially the same as the inter-pulse interval of the first sequence of pulses corresponding to the first electrical signal. Furthermore, the second inter-pulse interval is substantially the same as the inter-pulse interval of the sequence of conditioning pulses corresponding to the second electrical signal. At block 306, the generated sequence of stimulation pulses is delivered to the recipient via a single stimulation channel.

As would be appreciated, the above and other operations of the present invention may be implemented an application-specific integrated circuit (ASIC), or other hardware or combination of hardware and software, or software as deemed appropriate for the particular application. For example, operations in accordance with certain embodiments of the present invention may be implemented as software executing on a cochlear implant or other hearing prosthesis. In such embodiments, the program code and any other necessary information may be stored in any manner suitable for the particular application, including programmed in an ASIC or other computer hardware or as software code stored in computer or machine readable medium such as any non-volatile storage device well known to those skilled in the art. In such embodiments, the program code is executed by the hearing prosthesis to perform the desired operations.

Figure 4A:
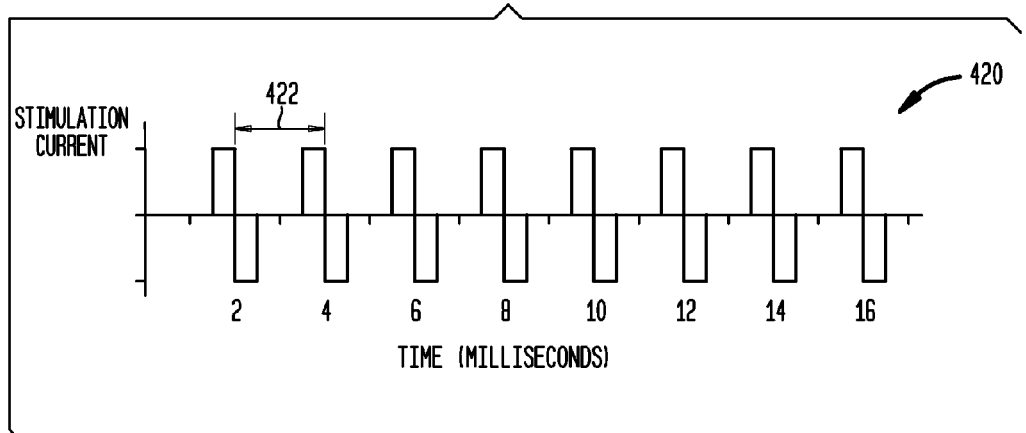
FIG. 4A is a graph of stimulation current versus time that illustrate the timing of pulses in stimulation signals generated in a cochlear implant in accordance with embodiments of the present invention.

As noted above, sound signal 207 is received by cochlear implant 200 and converted to one or more data signals 213. As noted, data signals 213 may be utilized by stimulator unit to generate sequences of electrical pulses. For example, a first data signal 213A is generated based on components 223A of sound signal 207 corresponding to a first pitch. Data signal 213A is usable by stimulator unit 206 to generate a sequence of electrical stimulation pulses having a substantially constant inter-pulse interval that is based on the first pitch. Similarly, a second data signal 213B is generated based on components 223B of sound signal 207 corresponding to a second pitch. Data signal 213B is usable by stimulator unit 206 to generate a sequence of electrical stimulation pulses having a substantially constant inter-pulse interval that is based on the second pitch. FIG. 4A is a graph of stimulation current versus time illustrating the timing of pulses in an exemplary pulse sequence that is generated using signal 213A. Furthermore, FIG. 4B is a graph of stimulation current versus time illustrating the timing of pulses in an exemplary pulse sequence that is generated using signal 213B.

In FIG. 4A, stimulation signal 420 corresponding to signal 213A comprises a sequence of digital pulses each spaced in time from adjacent pulses by an inter-pulse interval 422 of approximately 2 ms. The substantially constant inter-pulse interval is based on a first pitch of sound signal 207. The pulses each comprise a bi-phasic pulse of stimulation current. However, in other embodiments, additional pulse types may be used.

Figure 4B:
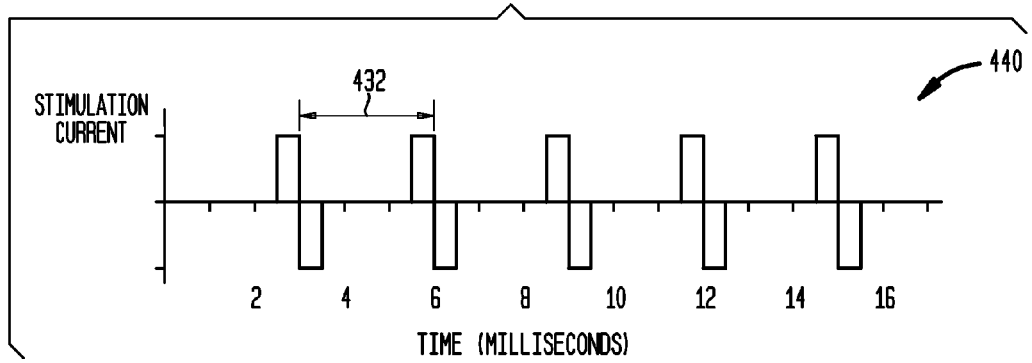
FIG. 4B is a graph of stimulation current versus time that illustrate the timing of pulses in stimulation signals generated in a cochlear implant in accordance with embodiments of the present invention.

In FIG. 4B, stimulation signal 440 corresponding to signal 213B comprises a sequence of digital pulses each spaced in time from adjacent pulses by an inter-pulse interval 432 of approximately 3 ms. The substantially constant inter-pulse interval is based on a second pitch of sound signal 207. The pulses each comprise a bi-phasic pulse of stimulation current. However, in other embodiments, additional pulse types may be used.

Figure 4C:
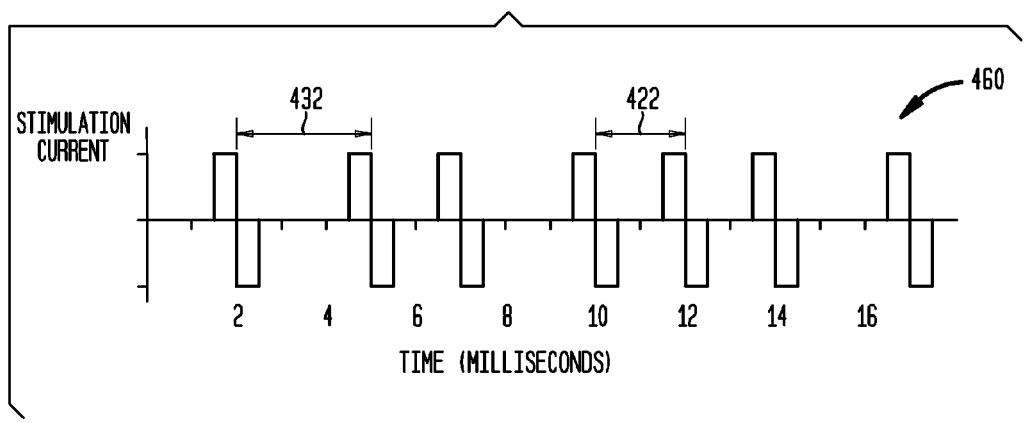
FIG. 4C is a graph of stimulation current versus time that illustrates the timing of pulses within a stochastic stimulation signal generated based on the signals of FIGS. 4A and 4B, in accordance with embodiments of the present invention.

FIG. 4C is a graph of stimulation current versus time that illustrates the timing of pulses within a stochastic stimulation sequence 460 generated by stochastic stimulation generator 216 of FIG. 2B. In this embodiment, stochastic stimulation sequence 460 is generated by combining stimulation signals 420 and 440. Stimulation signals 420 and 440 are combined in a manner such that inter-pulse intervals 422, 432 are distributed stochastically throughout stimulation sequence 460. For example, in the embodiment of FIG. 4C, the inter-pulse intervals between pulses of stochastic stimulation sequence 460 vary between 2 ms and 3 ms. In the exemplary embodiment of FIG. 4C, a first pulse occurs at time 2 ms, followed by pulses at 5 ms (inter-pulse interval of 3 ms), 7 ms (inter-pulse interval of 2 ms), 10 ms (inter-pulse interval of 3 ms), 12 ms (inter-pulse interval of 2 ms), 14 ms (inter-pulse interval of 2 ms), 16 ms (inter-pulse interval of 2 ms), etc. This random variation of inter-pulse intervals between pulses continues throughout the entirety of stochastic stimulation sequence 460.

As noted above, the pulse timing within stochastic stimulation sequence 460 varies at random between inter-pulse intervals 422 and 432 within controlled limits. For example, in certain embodiments, the number of consecutive pulses having the same inter-pulse interval there between may be limited. In other embodiments, the distribution of inter-pulse intervals within stochastic stimulation sequence 460 may need to be substantially balanced throughout the signal, or alternatively, the number of inter-pulse intervals 422 or 432 may weighted to adjust the resulting hearing perception. In certain embodiments, such as the embodiment described above, first and second inter-pulse intervals are present in a stochastic stimulation signal. In these embodiments, the inter-pulse intervals between pulses may not continually alternate between the first and second inter-pulse intervals.

As noted above, delivery of a stochastic stimulation signal 460 to a recipient causes a recipient to perceive multiple pitches within a single stimulation sequence. For example, in FIG. 4C, stochastic stimulation sequence 460 corresponds to signals 213A, 213B used to generate stimulation signals 420 and 440. Due to the fact that multiple pitches may be perceived by the recipient, one sound source from which signal 420 was generated may be associated with a first perceived pitch and a second source from which signal 440 was generated may be associated with a second perceived pitch. In these embodiments, upon delivery of stochastic stimulation sequence 460, the perception of the multiple pitches each associated with a particular source by the recipient may result in the recipient's ability to differentiate between the two sources.

In alternative embodiments of the present invention, a conditioning stimulus and a sound signal corresponding to a received sound may be encoded within a single stochastic stimulation sequence so as to cause sound perception and rate conditioning within a single sequence.

Figure 5:
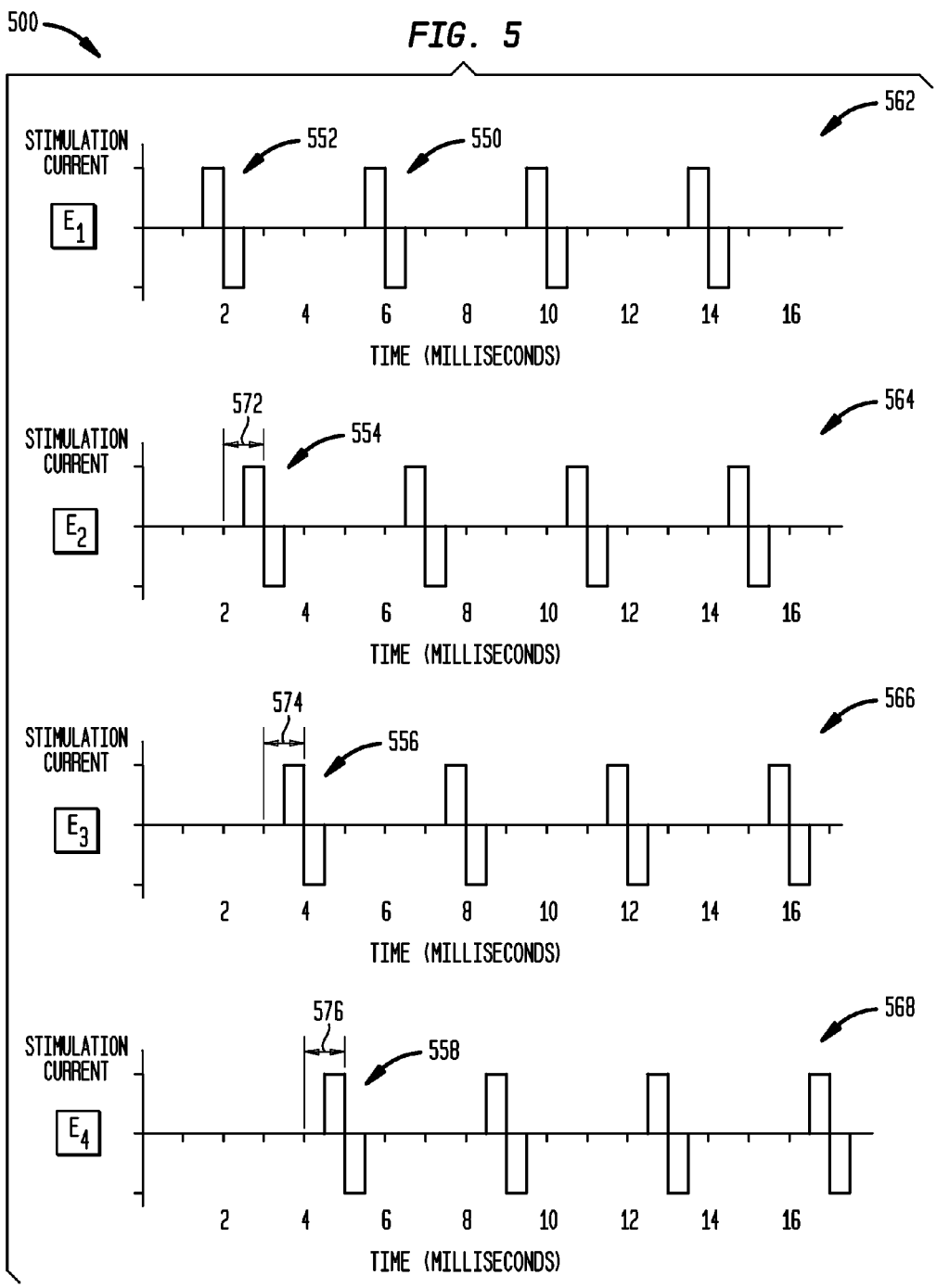
FIG. 5 is a graph of stimulation current versus time that illustrates the delivery of a stimulation signal to a cochlea of a recipient via four electrodes of a cochlear implant in accordance with embodiments of the present invention.

A cochlear implant may deliver electrical stimulation signals to a recipient via a plurality of electrodes. FIG. 5 is a graph of stimulation current versus time that illustrates the delivery of a stimulation signal 500 to a recipient's cochlea via four electrodes of a cochlear implant, illustrated as electrodes E1, E2, E3 and E4.

As shown in FIG. 5, a sequence of pulses 562 is delivered to a portion of the cochlea via electrode E1. Pulses within sequence 562 are spaced in time from adjacent pulses by a substantially constant inter-pulse interval of 4 ms. A first pulse 552 in sequence 562 occurs at time 2 ms.

Stimulation signal 500 further comprises a sequence 564 of pulses delivered to a portion of the cochlea via electrode E2. Similar to sequence 562, pulses within sequence 564 are spaced in time from adjacent pulses by a substantially constant inter-pulse interval of 4 ms. As shown, the delivery of a first pulse 554 in sequence 564 is delayed by a time interval 572 from the delivery of first pulse 552 of sequence 562. In the embodiment of FIG. 5, this delay comprises approximately 1 ms.

Stimulation signal 500 also comprises sequences 566 and 568 of pulses delivered to portions of the cochlea via electrodes E3, 34 respectively. Similar to sequences 562 and 564, pulses within sequences 566 and 568 are spaced in time by a substantially constant inter-pulse interval of 4 ms. The delivery of a first pulse 556 of sequence 566 is delayed by 1 ms from the delivery of pulse 554. Likewise, the delivery of a first pulse 558 of sequence 568 is delayed by 1 ms from the delivery of pulse 556. Following delivery of pulse 556, a second pulse 550 is delivered at electrode E1. The delivery of pulse 550 is also delayed by 1 ms from the delivery of pulse 558.

The above procedure of sequentially delivering delayed pulses at electrodes E1-E4 continues until all pulses within stimulation signal 500 have been delivered. Following delivery of stimulation signal 500, a next stimulation signal may be delivered to the cochlea.

As would appreciated by one of ordinary skill in the art, the perceived pitch of a sound refers to the cochlea's response to the frequency of a sound. The perception of pitch by an individual generally depends on place pitch perception. Place pitch perception refers to the cochlea's spatial sensitivity to frequency. Specifically, in a fully functional ear, high frequency sounds selectively vibrate the basilar membrane near the oval window, and lower frequency sounds travel further along the membrane before excitation of the membrane. Thus, the basic pitch determining mechanism of the cochlea is based on the location along the membrane where the hairs cells are stimulated.

Conventional cochlear implants have been designed to take advantage of this place pitch phenomenon of the cochlea. In these cochlear implants, the location at which stimulation is delivered to the cochlea is used to control the pitch perceived by a recipient. Stimulation signal 500 of FIG. 5 is an example of this type of stimulation. The pitch perceived by the recipient as a result of stimulation 500 depends on which electrodes E1-E4 are used. For example, a first pitch may be perceived when stimulation is delivered via all four electrodes, while an alternative pitch may be perceived when stimulation is delivered, for example, via electrodes E1 and E3 only. In contrast, as noted above, embodiments of the present invent exploit the ability of the cochlea to temporally segregate pitches. Specifically, as noted above, a stochastic sequence of electrical stimulation pulses is generated and delivered to the recipient via a single electrode. The sequence comprises pulses separated by two or more inter-pulse intervals that are distributed stochastically throughout the sequence within controlled limits. This controlled randomness in the pulse timing exploits the temporal pitch perception properties of the cochlea so that multiple pitches may be perceived as a result of the single stochastic pulse sequence. This ability may enhance speech processing and/or sound coding strategies implemented by a cochlear implant.

Figure 6A:
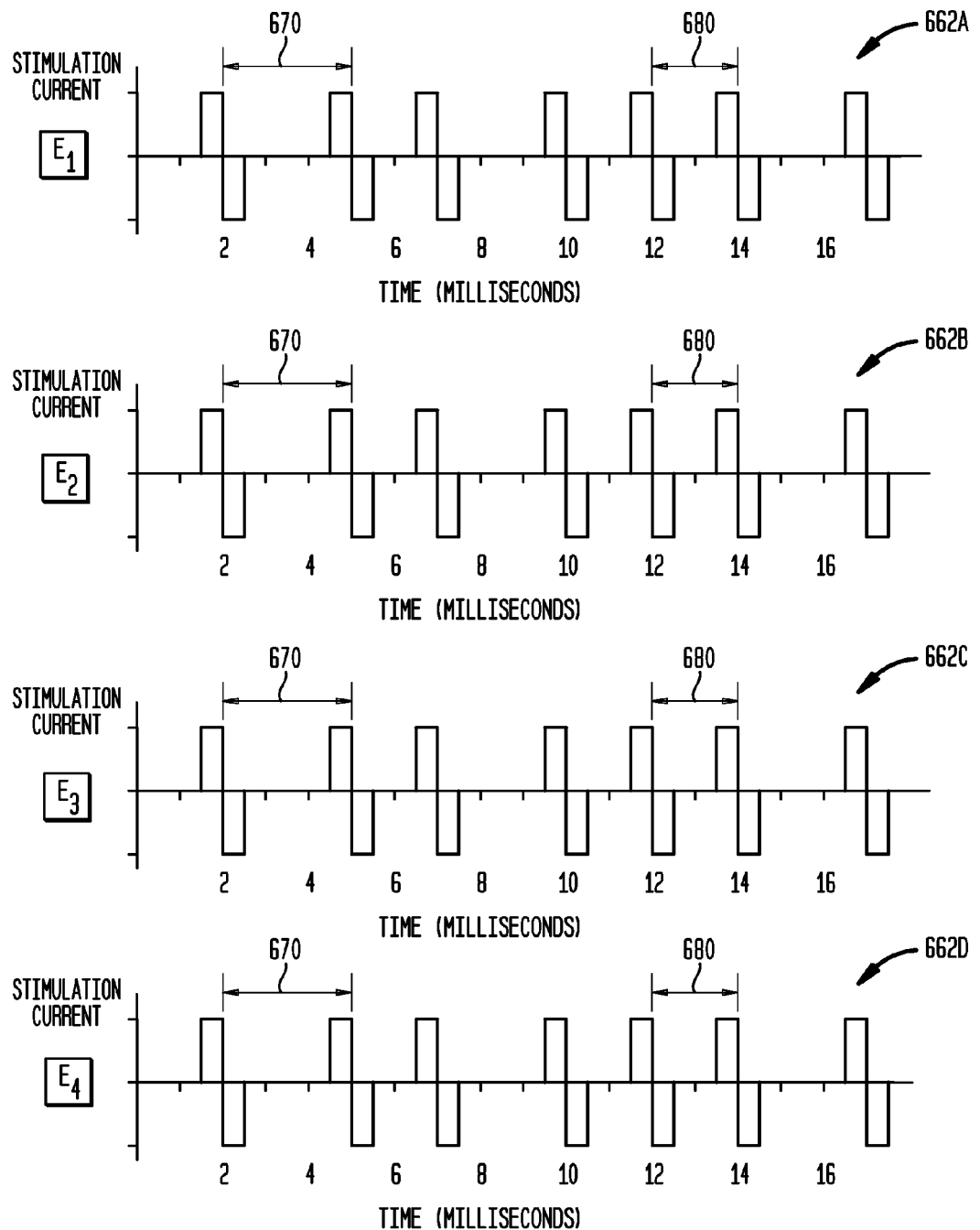
FIG. 6A is a graph of stimulation current versus time that illustrate the delivery of a synchronized stochastic stimulation signal to a cochlea of a recipient via four electrodes of a cochlear implant in accordance with embodiments of FIG. 2B.

In certain embodiments of the present invention, a stochastic sequence of electrical stimulation pulses may be synchronized for delivery via a plurality of electrodes. FIGS. 6A and 6B are graphs of stimulation current versus time that illustrate the delivery of synchronized stochastic stimulation sequences to a recipient's cochlea via four electrodes E1-E4.

In the embodiments illustrated in FIG. 6A stochastic stimulation sequences 662 are applied to each of electrodes E1-E4. Similarly, in the embodiments illustrated in FIG. 6B stochastic stimulation sequences 664 are applied to each of electrodes E1-E4. Stochastic sequences 662 and 664 are substantially the same as sequence 460 of FIG. 4C. Thus, the inter-pulse intervals and interval distribution within each sequence 662, 664 correspond directly to the inter-pulse intervals and pulse distribution of stochastic stimulation sequence 460. For example, as described above with reference to FIG. 4C, stochastic stimulation sequence 460 comprises a sequence of pulses each spaced in time from adjacent pulses by a controllably random inter-pulse interval. As noted, the inter-pulse intervals of stochastic stimulation sequence 460 are stochastically varied, within controlled limits, between 2 ms and 3 ms. In the embodiments of FIGS. 6A and 6B, the inter-pulse intervals between pulses within a given sequence are also varied between 2 ms and 3 ms in the same manner as in stochastic stimulation sequence 460.

In the embodiment of FIG. 6A, the pulse sequences are delivered to the cochlea via electrodes E1-E4 simultaneously. As shown in FIG. 6A, a first pulse is applied to electrodes E1-E4 at 2 ms. After a time interval 670, a second pulse is delivered simultaneously to electrodes E1-E4. Simultaneous pulse delivery continues until all pulses in the sequences have been delivered.

FIG. 6B illustrates alternative embodiments in which sequential pulse delivery is utilized for pulse sequences 664. As shown in FIG. 6B, a sequences of pulses 664 is delivered via electrodes E1-E4 sequentially. Pulses within sequences 664 are spaced in time by inter-pulse intervals directly corresponding to the inter-pulse intervals of stochastic stimulation sequence 460. The first pulse in sequence 664A occurs at time 2 ms.

The above embodiments illustrated in FIGS. 6A and 6B provide examples of synchronized stochastic stimulation. It should be appreciated that other embodiments are within the scope of the present invention. For example, in certain embodiments, cochlear implant 200 may include more or less than four electrodes. For example, in specific embodiments, cochlear implant 200 may include 22 electrodes. In these embodiments, the stochastic stimulation sequence may be applied via any number of electrodes.

Figure 7A:
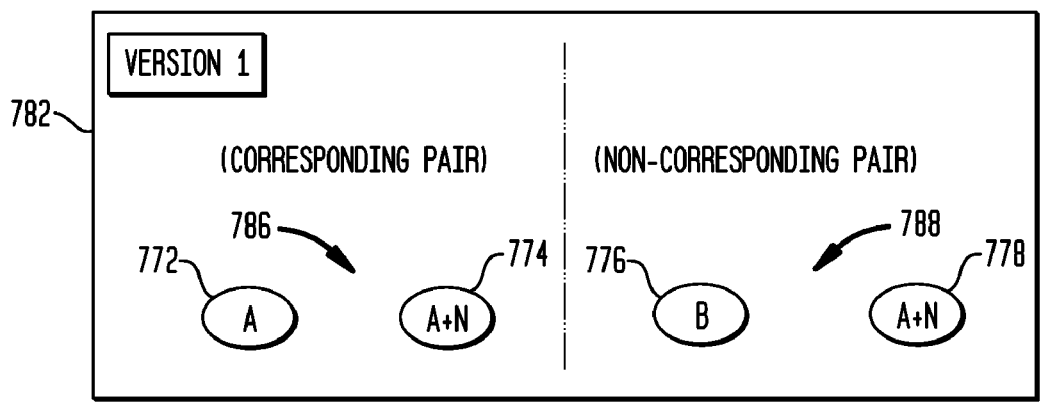
FIG. 7A is a schematic diagram illustrating sound signal pairs delivered to a recipient in accordance with embodiments of the present invention.
Figure 7B:
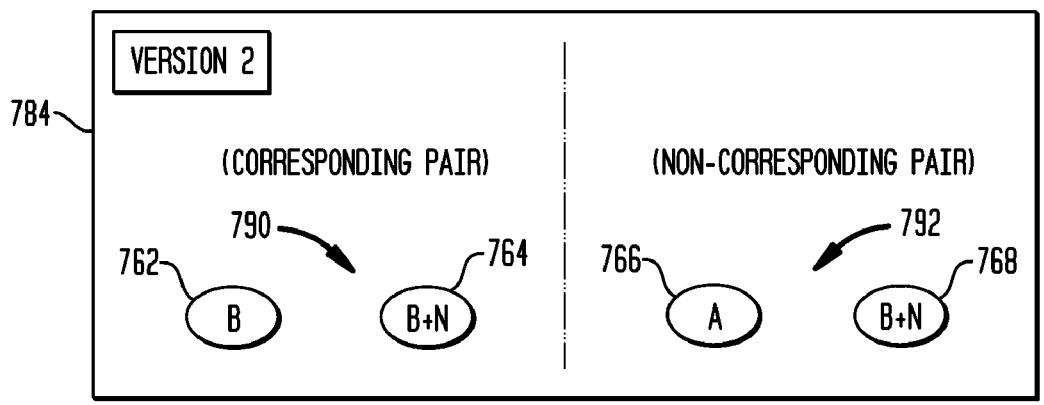
FIG. 7B is a schematic diagram illustrating sound signal pairs delivered to a recipient in accordance with embodiments of the present invention.

FIGS. 7A and 7B are schematic diagrams illustrating sound signal pairs delivered to a recipient in accordance with embodiments of a method described below with reference to FIGS. 8A and 8B. FIG. 7A illustrates a first version 782 of a sound signal pair, while FIG. 7B illustrates a second version 784 of a sound signal pair. For ease of illustration, the following discusses sound pairs based on a first signal A, a second signal B and a third signal N. Presentation of first signal A to the recipient results in the perception of pitch A, while presentation of second signal B to the recipient results in the perception of pitch B by the recipient. Signal N comprises a noise signal causing a perception of a pitch N by the recipient.

As described herein, sound pairs 786, 788, 790 and 792 may comprise acoustic or electrical representations of signals A, B and N. For example, in certain embodiments, sound signal 772 may comprise a sequence of electrical pulses which causes the recipient to perceive pitch A, while sound signal 774 may comprise a sequence of electrical pulses which causes the recipient to perceive pitch A mixed with pitch N.

In the embodiment of FIG. 7A, sound pair version 782 includes a corresponding sound pair 786 and a non-corresponding sound pair 788. Corresponding pair 786 comprises a first sound signal 772 which results in the perception of a pitch A and a second sound signal 774. Second sound signal 774 comprises a sound signal resulting in the perception of pitch A and pitch N. Non-corresponding pair 788 comprises a first sound signal 776 resulting in the perception of pitch B and a second sound signal 778. Second sound signal 778 comprises a sound signal resulting in the perception of pitch A and pitch N. Details of how these sound pair versions are used in the present invention are provided below with reference to FIGS. 8A and 8B.

In the embodiment of FIG. 7B, sound pair version 784 includes a corresponding sound pair 790 and a non-corresponding sound pair 792. In this embodiment, corresponding pair 790 comprises a first sound signal 762 resulting in the perception of a pitch B and a second sound signal 764. Second sound signal 764 comprises a sound signal resulting in the perception of pitch B and pitch N. Non-corresponding pair 792 comprises a first sound signal 766 resulting in the perception of a pitch A and a second sound signal 768. Second sound signal 768 comprises a sound signal resulting in the perception of pitch B and pitch N. Details of how these sound pair versions are used in the present invention are provided below with reference to FIG. 8.

Figure 8:
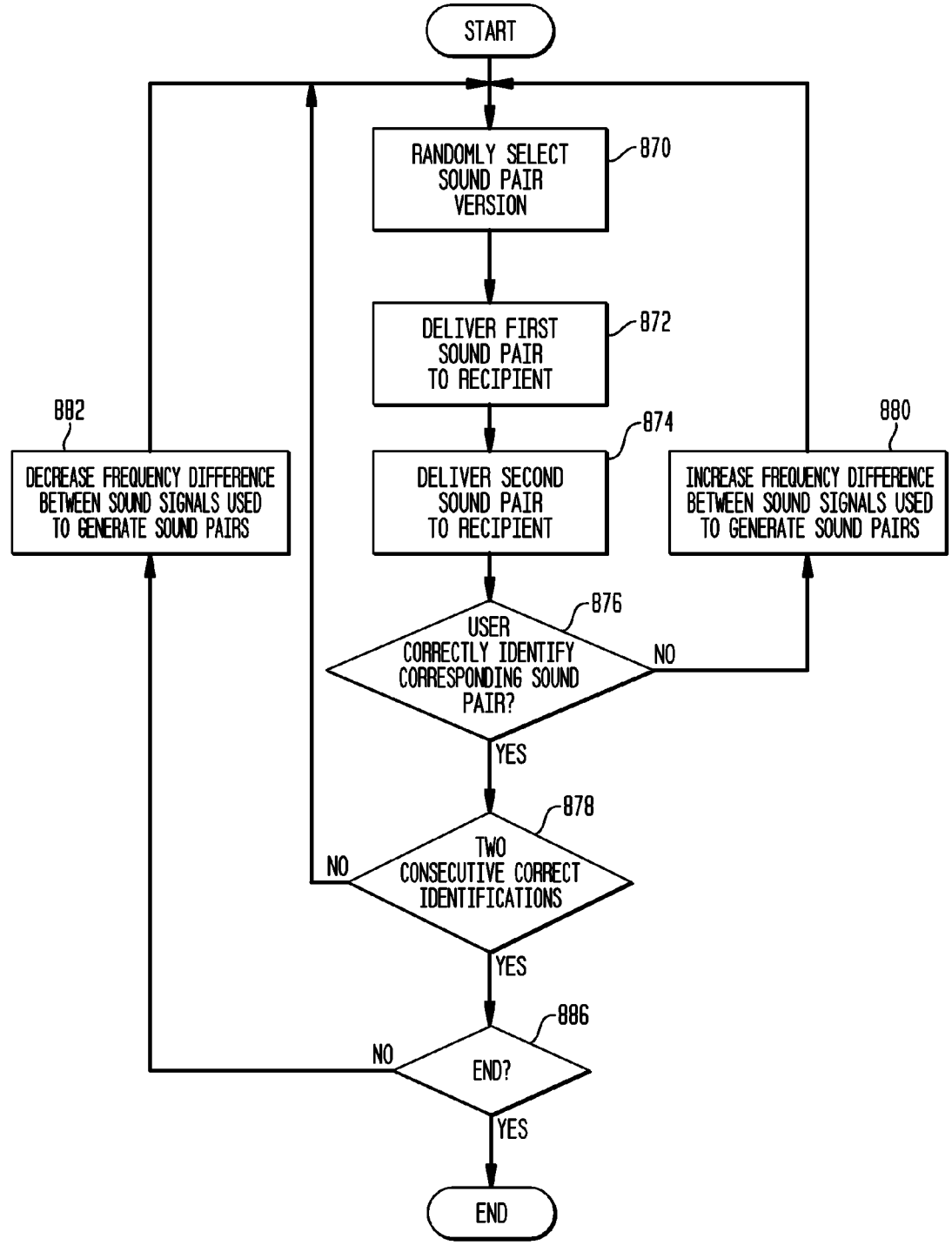
FIG. 8 is a flowchart illustrating a method for determining a recipient's ability to perceive differences in pitch between delivered sound signals in accordance with embodiments of the present invention.

FIG. 8 illustrates one exemplary method for determining a recipient's ability to perceive differences in pitch between delivered signals in accordance with embodiments of the present invention. The method of FIG. 8 is described herein with respect to a cochlear implant. However, it should be appreciated that the method of FIG. 8 may also be used with other hearing prosthesis, such as a hearing aid.

As shown in FIG. 8, at block 870 either first or second pair version 782, 784 discussed above is randomly selected for presentation to a recipient. At block 872, a first sound signal pair of the selected sound pair version is presented to the recipient. For ease of illustration, the method of FIG. 8 will be discussed with reference to presentation of version 782 of FIG. 7A. However, it should be appreciated that other versions may also be presented.

At block 870, corresponding pair 786 is presented to the recipient. This step comprises presenting sound signal 772 to the recipient, then separately presenting sound signal 774 to the recipient. Following presentation of corresponding pair 786, at block 872, non-corresponding pair 788 is presented to the recipient. This step comprises presenting sound signal 776 to the recipient, then separately presenting sound signal 778 to the recipient.

Following presentation of both sound signal pairs 786, 788, at block 876 the recipient must determine, based on the perceived pitches, if the presented sounds within corresponding sound pair 786, or the presented sounds within non-corresponding sound pair 788 sounded more similar to one another. As noted above, pitch is the cochlea's response to a frequency of a sound. As such, a correct identification by the recipient that the sound signals of corresponding sound pair 786 sounded more similar indicates that the recipient is able to perceive the frequency difference between signal A and signal B. An incorrect identification indicates that the recipient is unable to perceive the frequency difference between signals A and B.

If the recipient incorrectly identifies the sound signals of non-corresponding pair 788 as sounding more similar to one another, the method continues to block 880 where the sound signal pairs are adjusted. At block 870, the frequency difference between sound signals A and B is increased and new sound pair versions are generated. Following this increase, the method then returns to block 870 to randomly select a sound signal version and to present the adjusted sound signal pairs to the recipient. An increase in the frequency difference between signals A and B increases the likelihood that the recipient will correctly identify the corresponding pair.

Returning to block 876, if the recipient correctly identifies the corresponding pair, a check is done at block 878 to determine if the recipient has correctly identified the corresponding pair twice at a given frequency difference between signals A and B. If the recipient has not completed two consecutive identifications in a row, the method returns to block 870 to randomly select the sound pair version, and to reapply the sounds of the selected version at blocks 872 and 870.

If the recipient has completed two consecutive identifications of corresponding pair 786 at a given frequency difference between signals A and B, then the method continues to block 882. At block 882, the frequency difference between signals A and B are decreased, thereby making it more difficult for a recipient to perceive differences in the frequency. The utilized sound pairs may be adjusted to correspond to this new frequency difference and the above procedure may then be re-performed to determine if the recipient can perceive the frequency difference between adjusted signals A and B.

The above described method may be described as an adaptive staircase approach for determining a recipient's ability to perceive frequency differences in two sounds. This method may be referred to as an adaptive staircase approach because a two up, one down adjustment is implemented. In other words, as described above, if a recipient incorrectly identifies the non-corresponding pair a single time, the frequency difference between sound signals A and B are increased to make it easier for the recipient to perceive the frequency difference. However, a recipient must correctly identify the corresponding sound pair twice prior to decreasing the frequency difference between signals A and B. This adaptive staircase increases the accuracy of the above method as compared to an approach that increases or decreases the frequency difference between signals A and B based on a single response.

As noted above, the method described above with reference to FIG. 8 may be utilized in embodiments of the present invention to determine an individual recipients' ability to perceive frequencies differences in two sounds signals. This information may be used, for example, to fit a cochlear implant implementing embodiments of the present invention.

The method of FIG. 8 has been provided for illustration purposes only. It should be appreciated that other methods may be used to determine a user's ability to perceive frequency differences in two sound signals and/or to fit a cochlear implant implementing embodiments of the present invention to a recipient.

Although the present invention is described herein with respect to the generation of a stochastic stimulation signal by combining two or more stimulation signals, it should be appreciated that the above description has been provided for illustration purposes. Other methods for generating a stochastic stimulation signal are within the scope of the present invention. For example, in certain embodiments, a stochastic stimulation signal may be generated directly from digital signals rather than from stimulation signals generated by a signal processor.

Furthermore, while various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:

1. A method for providing a hearing percept to a recipient of a cochlear implant comprising:
    receiving a sound signal having at least one pitch;
    generating a stochastic sequence of electrical stimulation pulses having first and second inter-pulse intervals distributed stochastically throughout the sequence within controlled limits, the first inter-pulse interval being based on the at least one pitch; and
    delivering the generated stochastic sequence to the recipient via a single stimulation channel of the cochlear implant.

2. The method of claim 1, wherein the received sound signal has two or more pitches, and wherein generating the stochastic sequence of electrical stimulation pulses comprises:
    generating a stochastic sequence of electrical stimulation pulses having first and second inter-pulse intervals distributed stochastically throughout the sequence within controlled limits, the first inter-pulse interval being based on a first pitch of the sound signal, and the second inter-pulse interval being based on a second pitch of the sound signal.

3. The method of claim 2, further comprising:
    generating a first electrical signal usable to generate a first sequence of electrical stimulation pulses having a substantially constant inter-pulse interval associated with the first pitch;
    generating a second electrical signal usable to generate a sequence of electrical stimulation pulses having a substantially constant inter-pulse interval associated with the second pitch; and
    generating the stochastic sequence of electrical simulation pulses based on the first and second electrical signals, wherein the first inter-pulse interval is substantially the same as the inter-pulse interval of the first sequence of pulses corresponding to the first electrical signal, and wherein the second inter-pulse interval is substantially the same as the inter-pulse interval of the second sequence of pulses corresponding to the second electrical signal.

4. The method of claim 2, wherein receiving the sound signal comprises:
    receiving sound from first and second sources, the first source having the first pitch and the second source having the second pitch.

5. The method of claim 1, wherein the cochlear implant is configured to deliver sequences of conditioning pulses to the recipient, and wherein generating the stochastic sequence of electrical stimulation pulses comprises:
    generating a stochastic sequence of electrical stimulation pulses having first and second inter-pulse intervals distributed stochastically throughout the sequence within controlled limits, the first inter-pulse interval being based on the at least one pitch of the sound signal, and the second inter-pulse interval being based on the pulse timing of a desired sequence of conditioning pulses having a substantially constant inter-pulse interval.

6. The method of claim 5, further comprising:
    generating a first electrical signal usable to generate a first sequence of electrical stimulation pulses having a substantially constant inter-pulse interval associated with the at least one pitch;
    generating a second electrical signal usable to generate the desired sequence of conditioning pulses; and
    generating the stochastic sequence of electrical simulation pulses based on the first and second electrical signals, wherein the first inter-pulse interval is substantially the same as the inter-pulse interval of the first sequence corresponding to the first electrical signal, and wherein the second inter-pulse interval is substantially the same as the inter-pulse interval of the sequence of conditioning pulses.

7. The method of claim 1, further wherein the stochastic sequence of electrical stimulation pulses further comprises at least a third inter-pulse interval, and wherein the first, second and at least third inter-pulse intervals are distributed stochastically throughout the sequence within controlled limits.

8. The method of claim 1, further comprising:
providing the generated stochastic sequence to a plurality of electrodes of the cochlear implant;
delivering the entire sequence to the recipient via each of the electrodes.

9. A cochlear implant, comprising:
a sound pickup component configured to receive a sound signal having at least one pitch;
a stochastic stimulation generator configured to generate a stochastic sequence of electrical stimulation pulses having first and second inter-pulse intervals distributed stochastically throughout the sequence within controlled limits, the first inter-pulse interval being based on the at least one pitch; and
an electrode assembly having a stimulation channel to deliver the sequence of electrical stimulation pulses to the recipient.

10. The cochlear implant of claim 9, wherein the received sound signal has two or more pitches, and wherein the implant further comprises
a sound processor configured to generate a first electrical signal usable to generate a first sequence of electrical stimulation pulses having a substantially constant inter-pulse interval associated with a first pitch of the sound signal, and configured to generate a second electrical signal usable to generate a sequence of electrical stimulation pulses having a substantially constant inter-pulse interval associated with a second pitch of the sound signal;
wherein the stochastic stimulation generator is configured to generate the stochastic sequence based on the first and second electrical signals, and wherein the first inter-pulse interval is substantially the same as the inter-pulse interval of the first sequence of pulses corresponding to the first electrical signal, and wherein the second inter-pulse interval is the same as the inter-pulse interval of the second sequence of pulses corresponding to the second electrical signal.

11. The cochlear implant of claim 10, wherein the sound pickup element is configured to receive sound generated by first and second sources, the first source having the first pitch and the second source having the second pitch.

12. The cochlear implant 9, wherein the cochlear implant is configured to deliver sequences of conditioning pulses to the recipient, and wherein the cochlear implant further comprises:
a sound processor configured to generate a first electrical signal usable to generate a first sequence of electrical stimulation pulses having a substantially constant inter-pulse interval associated with the at least one pitch; and
a conditioner configured to generate a second electrical signal usable to generate a desired sequence of conditioning pulses having a substantially constant inter-pulse interval;
wherein the stochastic stimulation generator is configured to generate the stochastic sequence based on the first and second electrical signals, and wherein the first inter-pulse interval is substantially the same as the inter-pulse interval of the first sequence corresponding to the first electrical signal, and wherein the second inter-pulse interval is substantially the same as the inter-pulse interval of the sequence of conditioning pulses.

13. The cochlear implant of claim 9, further wherein the stochastic sequence of electrical stimulation pulses further comprises at least a third inter-pulse interval, and wherein the first, second and at least third inter-pulse intervals are distributed stochastically throughout the sequence within controlled limits.

14. The cochlear implant of claim 9, wherein the electrode assembly comprises a plurality of electrodes, and wherein the implant further comprises:
a synchronization module configured to provide the entire stochastic sequence of stimulation pulses to each of two or more of the plurality of electrodes.

15. A computer program embodied on a machine readable medium stored in a cochlear implant for providing a hearing percept of a received sound signal having at least one pitch to a recipient of the cochlear implant, the program comprising:
code for generating a stochastic sequence of electrical stimulation pulses having first and second inter-pulse intervals distributed stochastically throughout the sequence within controlled limits, the first inter-pulse interval being based on the at least one pitch; and
code for delivering the generated stochastic sequence to the recipient via a single stimulation channel of the cochlear implant.

16. The computer program of claim 15, wherein the received sound signal has two or more pitches, and wherein the code for generating the stochastic sequence of electrical stimulation pulses comprises:
code for generating a stochastic sequence of electrical stimulation pulses having first and second inter-pulse intervals distributed stochastically throughout the sequence within controlled limits, the first inter-pulse interval being based on a first pitch of the sound signal, and the second inter-pulse interval being based on a second pitch of the sound signal.

17. The computer program of claim 16, further comprising:
code for generating a first electrical signal usable to generate a first sequence of electrical stimulation pulses having a substantially constant inter-pulse interval associated with the first pitch;
code for generating a second electrical signal usable to generate a sequence of electrical stimulation pulses having a substantially constant inter-pulse interval associated with the second pitch; and
code for generating the sequence of electrical simulation pulses based on the first and second electrical signals, wherein the first inter-pulse interval is substantially the same as the inter-pulse interval of the first sequence of pulses corresponding to the first electrical signal, and wherein the second inter-pulse interval is substantially the same as the inter-pulse interval of the second sequence of pulses corresponding to the second electrical signal.

18. The computer program of claim 15, wherein the cochlear implant is configured to deliver sequences of conditioning pulses to the recipient, and wherein the code for generating the stochastic sequence of electrical stimulation pulses comprises:
code for generating a stochastic sequence of electrical stimulation pulses having first and second inter-pulse intervals distributed stochastically throughout the sequence within controlled limits, the first inter-pulse interval being based on the at least one pitch of the sound signal, and the second inter-pulse interval being based on the pulse timing of a desired sequence of conditioning pulses having a substantially constant inter-pulse interval.

19. The computer program of claim 18, further comprising:
code for generating a first electrical signal usable to generate a first sequence of electrical stimulation pulses having a substantially constant inter-pulse interval associated with the at least one pitch;
code for generating a second electrical signal usable to generate the desired sequence of conditioning pulses; and code for generating the stochastic sequence of electrical simulation pulses based on the first and second electrical signals, wherein the first inter-pulse interval is substantially the same as the inter-pulse interval of the first sequence corresponding to the first electrical signal, and wherein the second inter-pulse interval is substantially the same as the inter-pulse interval of the sequence of conditioning pulses.

20. A method for providing a hearing percept to a recipient of a hearing prosthesis comprising:
receiving a sound signal having at least one pitch;
generating a stochastic sequence of stimulation pulses having first and second inter-pulse intervals distributed stochastically throughout the sequence within controlled limits, the first inter-pulse interval being based on the at least one pitch; and
delivering the generated stochastic sequence to the recipient via a single stimulation channel of the hearing prosthesis.

21. The method of claim 20, wherein the received sound signal has two or more pitches, and wherein generating the stochastic sequence of stimulation pulses comprises:
generating a stochastic sequence of stimulation pulses having first and second inter-pulse intervals distributed stochastically throughout the sequence within controlled limits, the first inter-pulse interval being based on a first pitch of the sound signal, and the second inter-pulse interval being based on a second pitch of the sound signal.

22. The method of claim 21, further comprising:
generating a first electrical signal usable to generate a first sequence of stimulation pulses having a substantially constant inter-pulse interval associated with the first pitch;
generating a second electrical signal usable to generate a sequence of stimulation pulses having a substantially constant inter-pulse interval associated with the second pitch; and
generating the stochastic sequence of simulation pulses based on the first and second electrical signals, wherein the first inter-pulse interval is substantially the same as the inter-pulse interval of the first sequence of pulses corresponding to the first electrical signal, and wherein the second inter-pulse interval is substantially the same as the inter-pulse interval of the second sequence of pulses corresponding to the second electrical signal.

23. The method of claim 21, wherein receiving the sound signal comprises:
receiving sound from first and second sources, the first source having the first pitch and the second source having the second pitch.

24. The method of claim 20, wherein the hearing prosthesis is configured to deliver sequences of conditioning pulses to the recipient, and wherein generating the stochastic sequence of stimulation pulses comprises:
generating a stochastic sequence of stimulation pulses having first and second inter-pulse intervals distributed stochastically throughout the sequence within controlled limits, the first inter-pulse interval being based on the at least one pitch of the sound signal, and the second inter-pulse interval being based on the pulse timing of a desired sequence of conditioning pulses having a substantially constant inter-pulse interval.

25. The method of claim 24, further comprising:
generating a first electrical signal usable to generate a first sequence of stimulation pulses having a substantially constant inter-pulse interval associated with the at least one pitch;
generating a second electrical signal usable to generate the desired sequence of conditioning pulses; and
generating the stochastic sequence of electrical simulation pulses based on the first and second electrical signals, wherein the first inter-pulse interval is substantially the same as the inter-pulse interval of the first sequence corresponding to the first electrical signal, and wherein the second inter-pulse interval is substantially the same as the inter-pulse interval of the sequence of conditioning pulses.

26. A hearing prosthesis, comprising:
a sound pickup component configured to receive a sound signal having at least one pitch;
a stochastic stimulation generator configured to generate a stochastic sequence of stimulation pulses having first and second inter-pulse intervals distributed stochastically throughout the sequence within controlled limits, the first inter-pulse interval being based on the at least one pitch; and
at least one stimulation channel to deliver the sequence of electrical stimulation pulses to the recipient.

27. The hearing prosthesis of claim 26, wherein the received sound signal has two or more pitches, and wherein the implant further comprises
a sound processor configured to generate a first electrical signal usable to generate a first sequence of stimulation pulses having a substantially constant inter-pulse interval associated with a first pitch of the sound signal, and configured to generate a second electrical signal usable to generate a sequence of stimulation pulses having a substantially constant inter-pulse interval associated with a second pitch of the sound signal;
wherein the stochastic stimulation generator is configured to generate the stochastic sequence based on the first and second electrical signals and wherein the first inter-pulse interval is substantially the same as the inter-pulse interval of the first sequence of pulses corresponding to the first electrical signal, and wherein the second inter-pulse interval is substantially the same as the inter-pulse interval of the second sequence of pulses corresponding to the second electrical signal.

28. The hearing prosthesis of claim 27, wherein the sound pickup element is configured to receive sound generated by first and second sources, the first source having the first pitch and the second source having the second pitch.

29. The hearing prosthesis of claim 26, wherein the hearing prosthesis is configured to deliver sequences of conditioning pulses to the recipient, and wherein the hearing prosthesis further comprises:
a sound processor configured to generate a first electrical signal usable to generate a first sequence of stimulation pulses having a substantially constant inter-pulse interval associated with the at least one pitch; and
a conditioner configured to generate a second electrical signal usable to generate a desired sequence of conditioning pulses having a substantially constant inter-pulse interval;
wherein the stochastic stimulation generator is configured to generate the stochastic sequence based on the first and second electrical signals, and wherein the first inter-pulse interval is substantially the same as the inter-pulse interval of the first sequence corresponding to the first electrical signal, and wherein the second inter-pulse interval is substantially the same as the inter-pulse interval of the sequence of conditioning pulses.

* * * * *